US00PP33955P2

(12) United States Plant Patent
Kleinwee

(10) Patent No.: US PP33,955 P2
(45) Date of Patent: Feb. 15, 2022

(54) ***PETUNIA* PLANT NAMED 'PEHY0064'**

(50) Latin Name: *Petunia hybrida*
Varietal Denomination: PEHY0064

(71) Applicant: SYNGENTA CROP PROTECTION AG, Basel (CH)

(72) Inventor: Theodorus Cornelis Maria Van Kleinwee, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/371,539

(22) Filed: Jul. 9, 2021

(51) Int. Cl.
*A01H 6/82* (2018.01)
*A01H 5/02* (2018.01)

(52) U.S. Cl.
USPC ..... Plt./356.1

(58) Field of Classification Search
USPC ..... Plt./356.1
See application file for complete search history.

*Primary Examiner* — Annette H Para
(74) *Attorney, Agent, or Firm* — Dale Skalla

(57) ABSTRACT

A new *Petunia* plant named 'PEHY0064' particularly distinguished by its medium to big sized flowers, yellow flower color, medium to late flowering and mounding plant habit.

1 Drawing Sheet

Latin name of the genus and species of the plant claimed: *Petunia hybrida.*

Varietal denomination: 'PEHY0064'.

BACKGROUND OF THE NEW PLANT

The present invention comprises a new *Petunia*, botanically known as *Petunia hybrida*, and hereinafter referred to by the variety name 'PEHY0064'.

'PEHY0064' is a product of a planned breeding program. The new cultivar has medium to big sized flowers, a yellow flower color, medium to late flowering and a mounding plant habit.

'PEHY0064' originated from a hybridization made in October 2016 in a controlled breeding environment in Enkhuizen, The Netherlands. The female parent was the variety 'Sanguna White', not patented. Compared to 'PEHY0064', it is more vigorous, is later flowering and has a white flower color.

The male parent of 'PEHY0064' was the variety 'Aurora Banana Candy', not patented. The male parent has yellow flower color, bit cup shaped flowers, medium sized flowers, late flowering, and mounding to upright plant habit.

The resulting seeds were sown in January 2017. 'PEHY0064' was selected as one flowering plant within the progeny of the stated cross in May 2017 in a controlled environment in Enkhuizen, The Netherlands.

The first act of asexual reproduction of 'PEHY0064' was accomplished when vegetative cuttings were propagated from the initial selection in June 2017 in a controlled environment in Enkhuizen, The Netherlands.

BRIEF SUMMARY OF INVENTION

Horticultural examination of plants grown from cuttings of the plant initiated in June 2016 and continuing thereafter, has demonstrated that the combination of characteristics as herein disclosed for 'PEHY0064' are firmly fixed and are retained through successive generations of asexual reproduction.

'PEHY0064' has not been observed under all possible environmental conditions. The phenotype may vary significantly with variations in environment such as temperature, light intensity, and day length.

A Plant Breeder's Right for this cultivar has not yet been applied for. 'PEHY0064' has not been made publicly available prior to the effective filing date of this application, notwithstanding any disclosure that may have been made less than one year prior to the effective filing date of this application by the inventor or another who obtained 'PEHY0064' directly from the inventor.

The following traits have been repeatedly observed and are determined to be basic characteristics of the new variety. The combination of these characteristics distinguishes this *Petunia* as a new and distinct variety.

BRIEF DESCRIPTION OF THE PHOTOGRAPHS

Figure 1:
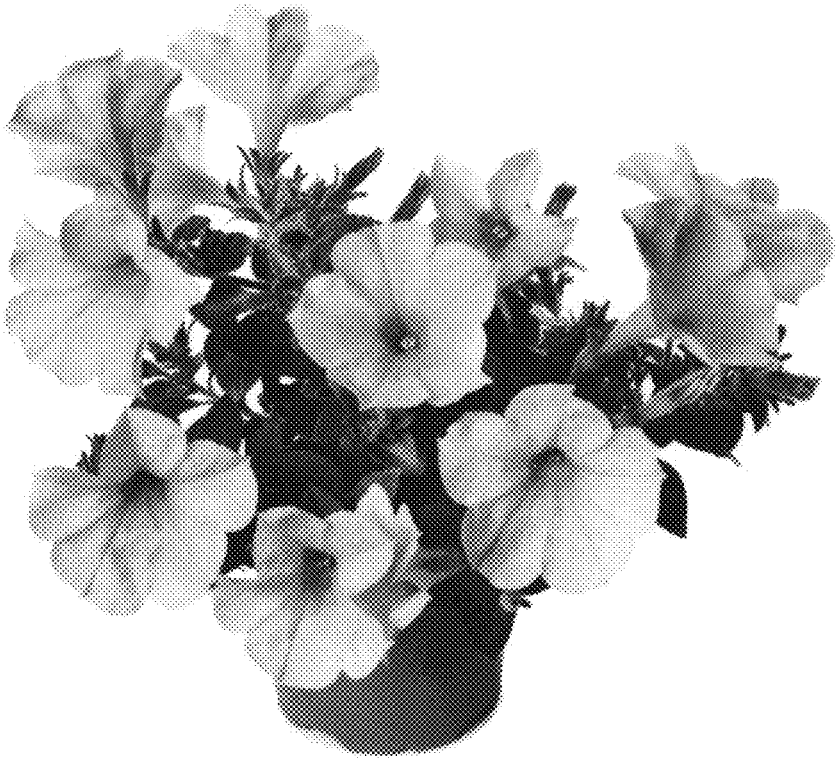
Figure 2:
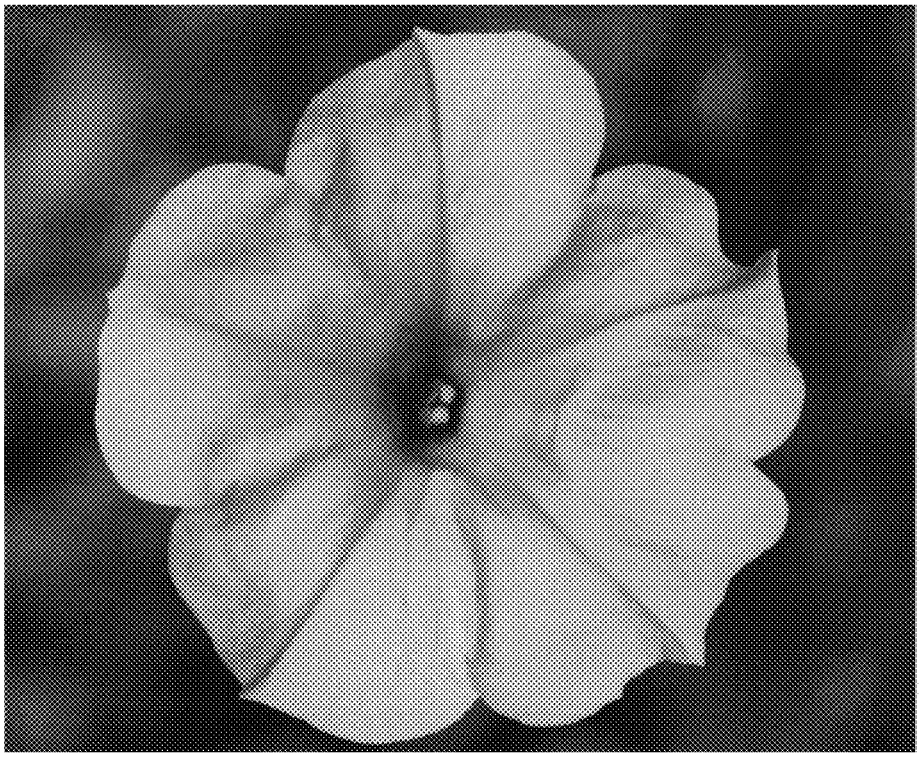

The accompanying photographic drawings show typical flower and foliage characteristics of 'PEHY0064' with colors being as true as possible with an illustration of this type. The photographic drawings show in FIG. 1 a flowering plant of the new variety and in FIG. 2 a close-up of the flowers.

DETAILED BOTANICAL DESCRIPTION

The aforementioned photographs were taken in May 2020 from plants growing indoor in 12 cm pots in Andijk, The Netherlands. These plants were approximately 12 weeks of age.

The plant descriptions and measurements were taken in June 2021 in Andijk, The Netherlands on outdoor plants grown in 35 cm containers. These plants were about 12 weeks old.

Color references are made to The Royal Horticultural Society Colour Chart (R.H.S.) 2001.

TABLE 1

DIFFERENCES BETWEEN THE NEW VARIETY 'PEHY0064' AND A SIMILAR VARIETY

| | 'PEHY0064' | 'Aurora Banana Candy', not patented |
|---|---|---|
| Earliness: | Bit earlier flowering | Late flowering |
| Flower size: | Medium to broad | Medium |
| Flower shape: | Flat | Bit cup shaped |

Plant:
- *Form, growth and habit.*—Mounding plant habit.
- *Plant height.*—15 cm.
- *Plant height (inflorescence included).*—17 cm.
- *Plant diameter (width).*—+/−24 cm.

Roots:
- *Number of days to initiate and produce roots.*—16 days at about 22° C.
- *Type.*—Fine, fibrous, free branching.
- *Color.*—RHS N158D.

Foliage:
- *Arrangement.*—Alternate, simple; sometimes opposite, decussate.
- *Immature leaf, color upper surface.*—RHS 137A.
- *Immature leaf, color lower surface.*—RHS 147B.
- *Mature leaf, color upper surface.*—RHS 137A.
- *Mature leaf, color lower surface.*—RHS 147B.
- *Length.*—3.5-4.5 cm.
- *Width.*—2-2.5 cm.
- *Shape.*—Ovate.
- *Base shape.*—Shortly attenuate.
- *Apex shape.*—Acute.
- *Margin.*—Entire.
- *Texture, upper surface.*—Densely covered with short hair.
- *Lower surface.*—Densely covered with short hairs.
- *Color of veins, upper surface.*—RHS 144B.
- *Color of veins, lower surface.*—RHS 144B.
- *Petiole color.*—RHS 144B.
- *Length.*—0.2 cm.
- *Diameter.*—0.2 cm.
- *Petiole texture.*—Densely covered with short hairs.

Stem:
- *Quantity of main branches per plant.*—4-5.
- *Color of stem.*—RHS 146B.
- *Length of stem.*—15 cm.
- *Diameter.*—0.3 cm.
- *Length of internodes.*—1.5-2.5 cm.
- *Texture.*—Dense, mostly glandular short hairs.
- *Color of pedicel.*—RHS 144B.
- *Length of pedicel.*—2.5 cm.
- *Diameter of pedicel.*—0.2 cm.
- *Texture of pedicel.*—Densely covered with short hairs.

Inflorescence:
- *Type.*—Flowers solitary in upper leaf axis.
- *Floret type.*—Funnel-shaped; 5 lobed petals; fused at base.
- *Blooming habit.*—Medium to late flowering in greenhouse, flowering throughout the summer months.
- *Quantity of inflorescences per plant.*—Approximately 30.
- *Lastingness of individual blooms on the plant.*—About 7 days.
- *Fragrance.*—Rather strong smell.

Bud (just when opening):
- *Color.*—RHS 1B at top, RHS 149B in middle RHS 144B towards base.
- *Length.*—2.3 cm.
- *Width.*—0.4 cm.
- *Shape.*—Oblong.

Immature inflorescence:
- *Flower horizontal diameter.*—5.5 cm.
- *Color petals, upper surface.*—RHS 2B, RHS 163A near throat.
- *Color petals, lower surface.*—RHS 1B.

Mature flower:
- *Flower horizontal diameter.*—6.5 cm.
- *Flower height (vertical).*—4.0 cm.
- *Color upper surface.*—RHS 2C at margin, RHS 2B in middle, RHS 163A near throat.
- *Color lower surface.*—RHS 1B.
- *Conspicuousness of veins.*—Weak.
- *Apex shape.*—Acuminate.
- *Margin.*—Entire.
- *Waviness of margin.*—Medium.
- *Petal lobation.*—Medium.
- *Petal texture, upper surface.*—Smooth.
- *Petal texture, lower surface.*—Smooth, occasionally a short hair.
- *Corolla tube color outside.*—RHS 166D with veins N144C.
- *Corolla tube color inside.*—RHS 163B.
- *Conspicuousness of veins in tube.*—Medium.
- *Corolla tube length.*—2.4 cm.
- *Corolla tube texture, outside.*—Rather dense and short glandular hairs.
- *Corolla tube texture, inside.*—Glabrous.

Calyx:
- *Color of sepal, upper surface.*—RHS 137B.
- *Color of sepal, lower surface.*—RHS 137C.
- *Length.*—1.2 cm.
- *Width.*—0.3 cm.
- *Shape.*—Ensiform.
- *Apex shape.*—Acute.
- *Base.*—Fused.
- *Margins.*—Entire.
- *Texture, upper surface.*—Densely covered with short glandular hairs.
- *Lower surface.*—Densely covered with short glandular hairs.

Reproductive organs:
- *Pistil.*—1.
- *Length.*—2.2 cm.
- *Style color.*—RHS 149D.
- *Style length.*—1.7 cm.
- *Stigma color.*—RHS 149B.
- *Stamens.*—
- *Quantity per flower.*—5.
- *Color of filaments.*—RHS 157D.
- *Length filaments.*—2.0 cm.
- *Anther color.*—RHS 158C.
- *Anther length.*—0.2 cm.
- *Anther shape.*—Elliptical.
- *Color of pollen.*—RHS 158C.
- *Pollen amount.*—Abundant.
- *Fertility/seed set.*—Has not been observed on this hybrid.
- *Disease/pest resistance.*—Has not been observed on this hybrid.

What is claimed is:

1. A new and distinct variety of *Petunia* plant named 'PEHY0064' substantially as illustrated and described herein.

* * * * *